(12) United States Patent
Hasson et al.

(10) Patent No.: US 9,404,152 B2
(45) Date of Patent: Aug. 2, 2016

(54) MICROFLUIDIC FLOW MONITORING

(71) Applicant: Canon U.S. Life Sciences, Inc., Rockville, MD (US)

(72) Inventors: Kenton C. Hasson, Germantown, MD (US); Gregory A. Dale, Gaithersburg, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 13/836,301

(22) Filed: Mar. 15, 2013

(65) Prior Publication Data

US 2014/0272984 A1  Sep. 18, 2014

Related U.S. Application Data

(63) Continuation of application No. 12/359,436, filed on Jan. 26, 2009.

(51) Int. Cl.
| | |
|---|---|
| *C12P 19/34* | (2006.01) |
| *C12Q 1/68* | (2006.01) |
| *B01L 3/00* | (2006.01) |
| *G01F 1/704* | (2006.01) |
| *G05D 7/00* | (2006.01) |
| *G01F 1/708* | (2006.01) |
| *G01F 1/712* | (2006.01) |

(52) U.S. Cl.
CPC ............ *C12Q 1/686* (2013.01); *B01L 3/502746* (2013.01); *C12P 19/34* (2013.01); *G01F 1/704* (2013.01); *G01F 1/7086* (2013.01); *G01F 1/712* (2013.01); *G05D 7/00* (2013.01); *B01L 2200/143* (2013.01); *B01L 2300/0816* (2013.01)

(58) Field of Classification Search
CPC ..................................................... C12P 19/34
USPC ....................................................... 435/91.2
See application file for complete search history.

(56) References Cited

U.S. PATENT DOCUMENTS

| | | | |
|---|---|---|---|
| 3,403,554 A | 10/1968 | Chevalier et al. | |
| 4,829,448 A | 5/1989 | Balding et al. | |
| 4,890,500 A | 1/1990 | Giles | |
| 5,719,341 A | 2/1998 | Reynolds et al. | |
| 5,726,751 A | 3/1998 | Altendorf et al. | |
| 6,130,098 A | 10/2000 | Handique et al. | |
| 6,808,075 B2 | 10/2004 | Bohm et al. | |
| 6,911,183 B1 | 6/2005 | Handique et al. | |
| 6,960,437 B2 | 11/2005 | Enzelberger et al. | |
| 6,976,590 B2 | 12/2005 | Deshpande et al. | |
| 7,004,184 B2 | 2/2006 | Handique et al. | |
| 7,057,198 B2 | 6/2006 | Meinhart et al. | |
| 7,104,405 B2 | 9/2006 | Bohm et al. | |
| 7,629,124 B2* | 12/2009 | Hasson et al. | 435/6.11 |
| 7,645,581 B2* | 1/2010 | Knapp et al. | 435/6.12 |
| 8,232,094 B2* | 7/2012 | Hasson et al. | 435/286.5 |
| 2002/0123033 A1 | 9/2002 | Eyal et al. | |
| 2002/0166592 A1 | 11/2002 | Liu et al. | |
| 2003/0070677 A1 | 4/2003 | Handique et al. | |
| 2003/0150716 A1 | 8/2003 | Hua et al. | |
| 2003/0198523 A1 | 10/2003 | Bohm et al. | |
| 2003/0234210 A1 | 12/2003 | Deshpande et al. | |
| 2004/0075824 A1 | 4/2004 | Belenkii et al. | |
| 2004/0161772 A1 | 8/2004 | Bohm et al. | |
| 2005/0042639 A1 | 2/2005 | Knapp et al. | |
| 2005/0045479 A1 | 3/2005 | Weigl et al. | |
| 2005/0075683 A1 | 4/2005 | Miesel et al. | |
| 2005/0092658 A1 | 5/2005 | Bohm et al. | |
| 2005/0148082 A1 | 7/2005 | Gilbert et al. | |
| 2005/0182573 A1 | 8/2005 | Tripathi et al. | |
| 2005/0189225 A1 | 9/2005 | Liu et al. | |
| 2005/0213076 A1 | 9/2005 | Saegusa | |
| 2006/0046300 A1 | 3/2006 | Padmanabhan et al. | |
| 2006/0051214 A1 | 3/2006 | Ussing | |
| 2006/0163087 A1 | 7/2006 | Allen et al. | |
| 2006/0194331 A1 | 8/2006 | Pamula et al. | |
| 2007/0026421 A1 | 2/2007 | Sundberg et al. | |
| 2008/0003588 A1* | 1/2008 | Hasson et al. | 435/6 |

OTHER PUBLICATIONS

Lagall Y et al., "Single-Molecule DNA Amplification and Analysis in an Integrated Microfluidic Device," Analytical Chemistry, vol. 73, No. 3, (2001) pp. 565-570.
Kopp et al., "Chemical Amplification: Continuous-Flow PCR on a Chip," Science, vol. 280, (1998) pp. 1046-1048.
Park et al., "Cylindrical compact thermal-cycling device for continuous-flow polymerase chain reaction," Analytical Chemistry, vol. 75 (2003) pp. 6029-6033.

* cited by examiner

*Primary Examiner* — Suchira Pande

(57) ABSTRACT

The present invention relates to systems and methods of monitoring velocity or flow in channels, especially in microfluidic channels. In some embodiments, the present invention relates to systems and methods of monitoring velocity or flow rate in systems and methods for performing a real-time polymerase chain reaction (PCR) in a continuous-flow microfluidic system.

26 Claims, 7 Drawing Sheets

MICROFLUIDIC FLOW MONITORING

REFERENCE TO RELATED APPLICATIONS

The present application is a continuation of the U.S. application Ser. No. 12/359,436, filed on Jan. 26, 2009, published as U.S. Patent Publication No. 2010/0191482 on Jul. 29, 2010, the entire disclosure of which is incorporated herein by reference.

BACKGROUND

1. Field of the Invention

The present invention relates to systems and methods of monitoring velocity or flow in channels, especially in microfluidic channels. In some embodiments, the present invention relates to systems and methods of monitoring velocity or flow rate in systems and methods for performing a real-time polymerase chain reaction (PCR) in a continuous-flow microfluidic system.

2. Discussion of Background

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. PCR is perhaps the most well-known of a number of different amplification techniques.

PCR is a powerful technique for amplifying short sections of DNA. With PCR, one can quickly produce millions of copies of DNA starting from a single template DNA molecule. PCR includes a three phase temperature cycle of denaturation of DNA into single strands, annealing of primers to the denatured strands, and extension of the primers by a thermostable DNA polymerase enzyme. This cycle is repeated so that there are enough copies to be detected and analyzed. In principle, each cycle of PCR could double the number of copies. In practice, the multiplication achieved after each cycle is always less than 2. Furthermore, as PCR cycling continues, the buildup of amplified DNA products eventually ceases as the concentrations of required reactants diminish. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Real-time PCR refers to a growing set of techniques in which one measures the buildup of amplified DNA products as the reaction progresses, typically once per PCR cycle. Monitoring the accumulation of products over time allows one to determine the efficiency of the reaction, as well as to estimate the initial concentration of DNA template molecules. For general details concerning real-time PCR see *Real-Time PCR: An Essential Guide*, K. Edwards et al., eds., Horizon Bioscience, Norwich, U.K. (2004).

Several different real-time detection chemistries now exist to indicate the presence of amplified DNA. Most of these depend upon fluorescence indicators that change properties as a result of the PCR process. Among these detection chemistries are DNA binding dyes (such as SYBR® Green) that increase fluorescence efficiency upon binding to double stranded DNA. Other real-time detection chemistries utilize Foerster resonance energy transfer (FRET), a phenomenon by which the fluorescence efficiency of a dye is strongly dependent on its proximity to another light absorbing moiety or quencher. These dyes and quenchers are typically attached to a DNA sequence-specific probe or primer. Among the FRET-based detection chemistries are hydrolysis probes and conformation probes. Hydrolysis probes (such as the TaqMan probe) use the polymerase enzyme to cleave a reporter dye molecule from a quencher dye molecule attached to an oligonucleotide probe. Conformation probes (such as molecular beacons) utilize a dye attached to an oligonucleotide, whose fluorescence emission changes upon the conformational change of the oligonucleotide hybridizing to the target DNA.

A number of commercial instruments exist that perform real-time PCR. Examples of available instruments include the Applied Biosystems PRISM 7500, the Bio-Rad iCycler, and the Roche Diagnostics LightCycler 2.0. The sample containers for these instruments are closed tubes which typically require at least a 10 µl volume of sample solution. If the lowest concentrations of template DNA detectable by a particular assay were on the order of one molecule per microliter, the detection limit for available instruments would be on the order of tens of targets per sample tube. Therefore, in order to achieve single molecule sensitivity, it is desirable to test smaller sample volumes, in the range of 1-1000 nl.

More recently, a number of high throughput approaches to performing PCR and other amplification reactions have been developed, e.g., involving amplification reactions in microfluidic devices, as well as methods for detecting and analyzing amplified nucleic acids in or on the devices. Microfluidic systems are systems that have at least one channel through which a fluid may flow, which channel has at least one internal cross-sectional dimension, (e.g., depth, width, length, diameter) that is less than about 1000 micrometers. Typically, microchannels have a cross-sectional dimension of about 5 microns to about 500 microns and a depth of about 1 micron to about 100 microns. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones.

For example, Lagally et al. (*Anal Chem* 73:565-570 (2001)) demonstrated amplification and detection of single template DNA in a 280 nl PCR chamber. Detection of products was made post-PCR using capillary electrophoresis. On the other hand, Kopp et al. (*Science* 280:1046-1048 (1998)) demonstrated continuous-flow PCR using a glass substrate with a serpentine channel passing over three constant temperature zones at 95° C. (denature), 72° C. (extension), and 60° C. (annealing). The 72° C. zone was located in the central region and had to be passed through briefly in going from 95° C. to 60° C. Detection was made post-PCR using gel electrophoresis. Since this PCR technique is not based on heating the entire surfaces of the reaction vessel, the reaction rate is determined by a flow rate, not a heating/cooling rate. Neither of these references described real-time monitoring of the PCR reaction.

Park et al. (*Anal Chem* 75:6029-6033 (2003)) describe a continuous-flow PCR device that uses a polyimide coated fused silica capillary wrapped into a helix around three temperature-controlled blocks. Sample volumes were 2 µl. Detection was made post PCR using gel electrophoresis. Reference was made to the possibility of adapting their instrument for real-time PCR by using a capillary coated with PTFE instead of non-transparent polyimide. See also, Hahn et al. (WO 2005/075683).

Enzelberger et al. (U.S. Pat. No. 6,960,437) describe a microfluidic device that includes a rotary channel having three temperature zones. A number of integrated valves and pumps are used to introduce the sample and to pump it through the zones in a rotary fashion.

Knapp et al. (U.S. Patent Application Publication No. 2005/0042639) describe a microfluidic device. A planar glass chip with several straight parallel channels is disclosed. A mixture of target DNA and PCR reagents is injected into these channels. In a first embodiment, the channels are filled with this mixture and flow is stopped. Then the entire length of the channels is thermally cycled. After thermal cycling is completed, the channels are imaged in order to detect regions of fluorescence where DNA has been amplified. In a second embodiment, the PCR mixture flows continuously through the amplification zone as the temperature is cycled, and fluorescence is detected downstream of the amplification zone. Different degrees of amplification are achieved by altering the time spent in cycling, through changing distance traveled under cycling, and the like. It is worth noting that this method varies conditions (such as cycles experienced) for separate consecutive sample elements, rather than monitoring the progress of individual sample elements over time.

Hasson et al. (U.S. Patent Application Publication No. 2008/0003588), incorporated herein by reference, describes systems and methods for real-time PCR in a microfluidic channel, and more particularly for real-time PCR in a continuous-flow microfluidic system. In accordance with the systems and methods described in this published application, the velocity of the fluid in the microfluidic channel can be monitored and adjusted.

Liu et al. (U.S. patent application publication No. 2002/0166592) describes a chip system and method for flow rate monitoring. An air bubble is introduced into an isolation channel of a microfluidic system. The velocity of the air bubble is determined by optically detecting the presence of the air bubble as it passes two LED/photodiode pairs located on both sides of the isolation channel at a fixed distance apart. A chromium layer is present on the chip to block environmental light and other scattered light.

There is an interest in further developing microfluidic genomic sample analysis systems for detecting DNA sequences, including an interest in developing systems and methods for monitoring flow velocity and flow rate in microfluidic channels to maximize the reaction parameters.

SUMMARY OF THE INVENTION

The present invention relates to systems and methods of monitoring velocity or flow in channels, particularly in microfluidic channels. In some embodiments, the present invention relates to systems and methods of monitoring velocity or flow rate in systems and methods for performing a real-time polymerase chain reaction (PCR) in a continuous-flow microfluidic system.

Thus, in a first aspect, the present invention provides a system of monitoring flow velocity and flow rate in channels. In some embodiments, the system comprises a chip comprising at least one microfluidic channel, a fluid movement system for moving a fluid through a microfluidic channel, a flow marker introduction system for introducing a flow marker into a microfluidic channel, an illumination system for generating two measuring points, a detection system for measuring the movement of the flow marker within the channel between the two measuring points, and a flow calculation system for determining flow marker velocity and correlating velocity to flow rate. In some embodiments, the channel comprises a flow measuring region. In other embodiments, the fluid movement system is a pump or a vacuum. In further embodiments, the flow marker introduction system is a piezoelectric nozzle, a bubble jet head or sipper. In some embodiments, the flow marker is selected from the group consisting of a bubble, a semiconductor quantum dot, a polymer microbead, a fluorescent particle and a scattering metal particle.

In some embodiments, the microchannel has a width of about 5 microns to about 500 microns and a depth of about 1 micron to about 100 microns. In other embodiments, the microchannel has a width of about 20 microns to about 400 microns and a depth of about 5 microns to about 50 microns. In additional embodiments, the microchannel has a width of about 30 microns to about 250 microns and a depth of about 10 microns to about 20 microns. In further embodiments, the microchannel has a width of about 150 microns and a depth of about 10 microns. In some embodiments, the flow measuring region of the channel is the same width as the channel. In other embodiments, the flow measuring region of the channel is narrower compared to the remainder of the channel. In some embodiments, the microchannel in the flow measuring region has a width of about 5 microns to about 400 microns and a depth of about 1 micron to about 100 microns. In other embodiments, the microchannel in the flow measuring region has a width of about 10 microns to about 200 microns and a depth of about 5 microns to about 50 microns. In additional embodiments, the microchannel in the flow measuring region has a width of about 20 microns to about 100 microns and a depth of about 10 microns to about 20 microns. In further embodiments, the microchannel in the flow measuring region has a width of about 40 microns and a depth of about 10 microns.

In some embodiments, the illumination system includes a light source. In some embodiments, the illumination system generates two measuring points from one light source by backside reflection or internal reflection from the chip. In some embodiments, the light source is a laser. In other embodiments, the light source is an LED. In some embodiments, the detection system includes a lens and a detector. In some embodiments, the flow calculation system is a computer. In other embodiments, the computer also controls a data acquisition rate for detecting the movement of the flow marker.

In a second aspect, the present invention provides a method of monitoring flow velocity and flow rate in channels. In some embodiments, the method comprises moving a solution through a microfluidic channel in a chip, introducing a flow marker into the channel, illuminating the channel at two measuring points, measuring the movement of the flow marker within the channel between the two measuring points and correlating the optical flow marker movement velocity to flow rate. In some embodiments, the microchannel has the dimensions described above. In some embodiments, the movement of the flow marker is measured in a flow measuring region of the channel. In some embodiments, the flow measuring region of the channel is the same width as the channel. In other embodiments, the flow measuring region of the channel is narrower compared to the remainder of the channel. In some embodiments, the dimensions of the microchannel in the flow measuring region have the dimensions described above.

In some embodiments, the flow marker is selected from the group consisting of a bubble, a semiconductor quantum dot, a polymer microbead, a fluorescent particle and a scattering metal particle. In some embodiments, the flow marker is a bubble that is introduced into the channel by injection, and the bubble is injected air formed by a piezoelectric nozzle. In other embodiments, the flow marker is a bubble that is formed by a bubble jet head to produce a vapor bubble.

In some embodiments, the illumination of the two measuring points is generated from one light source by a backside reflection or internal reflection from the chip. In some embodiments, the light source is a laser. In other embodiments, the light source is an LED. In some embodiments, one of the illumination points is internal reflection from the chip. In some embodiments, the reflection is caused naturally from the backside of the chip by internal reflection caused by the refractive index difference between the chip material and air. In other embodiments, the reflection is caused or enhanced by a reflective coating on one side of the chip. In additional embodiments, the reflective coating on the chip is co-integral with a flow measuring region within the channel. In some embodiments, the angle of incidence of the illumination is from about 30 degrees to about 60 degrees. In another embodiment, angle of incidence of the illumination is preferably about 45 degrees.

In some embodiments, the measurement of the flow marker involves fluorescence. In other embodiments, the illumination is an excitation signal. In some embodiments, the measurement of the flow marker involves a detection system. In some embodiments, the detection system includes a lens and a detector.

In some embodiments, the correlation of velocity to flow rate is performed by a computer. In some embodiments, the computer also controls a data acquisition rate for measuring the movement of the flow marker. In other embodiments, the flow rate measurement is part of a feedback loop for regulating the flow rate. In other embodiments, the illumination involves an optical signal that is scatter and/or reflection that is resolvable from natural background signal.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements.

DETAILED DESCRIPTION OF THE INVENTION

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, N.Y., Gait, *Oligonucleotide Synthesis: A Practical Approach*, 1984, IRL Press, London, Nelson and Cox (2000), Lehninger, *Principles of Biochemistry* 3rd Ed., W. H. Freeman Pub., New York, N.Y. and Berg et al. (2002) *Biochemistry*, 5th Ed., W. H. Freeman Pub., New York, N.Y., all of which are herein incorporated in their entirety by reference for all purposes.

As described above, the present invention provides systems and methods of monitoring velocity or flow in channels, particularly in microfluidic channels, and more particularly in systems and methods for performing a real-time polymerase chain reaction (PCR) in a continuous-flow microfluidic system.

Figure 1:
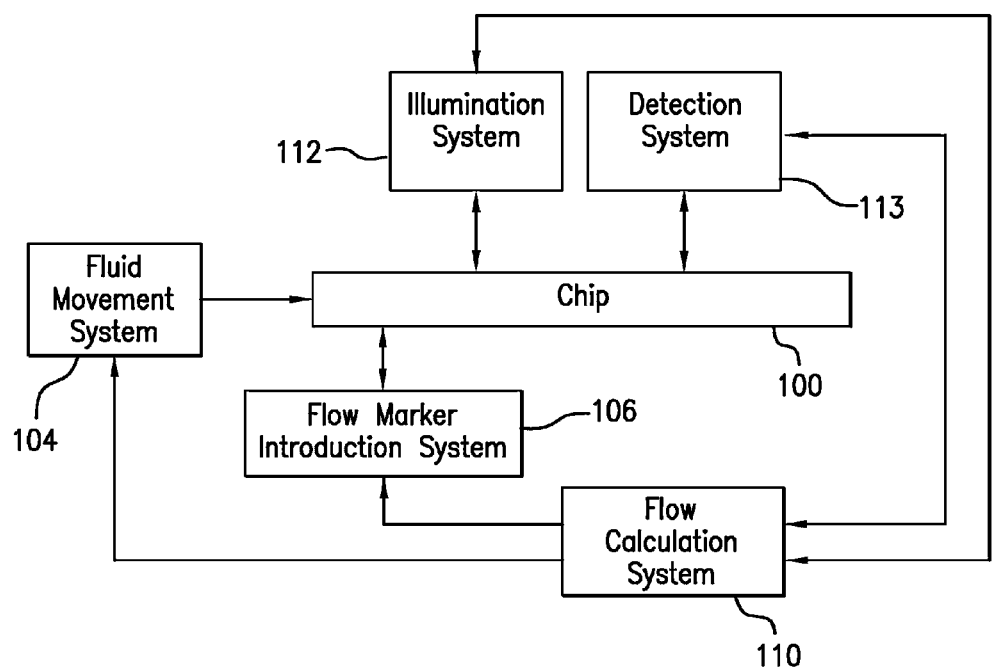
FIG. 1 is a diagram illustrating a system according to an embodiment of the present invention.

As shown in FIG. 1, an aspect of the present invention provides a system of monitoring flow velocity and flow rate in channels, particularly in microfluidic channels. The system comprises a chip 100 comprising at least one microfluidic channel, a fluid movement system 104 for moving a fluid through a microfluidic channel, a flow marker introduction system 106 for introducing a flow marker into a microfluidic channel, an illumination system 112 for generating at least two measuring points, a detection system 113 for measuring the movement of the flow marker within the channel between the measuring points, and a flow calculation system 110 for determining flow marker velocity and correlating velocity to flow rate. In one embodiment, fluid movement system 104 is a pump or a vacuum. Flow marker introduction system 106 is a piezoelectric nozzle, a bubble jet head or sipper. Flow marker introduction system 106 may include a converging inlet channel comprising a valve. It may also comprise a directed energy source that induces a measureable property change in the contents of the channel, for example, a heat source to induce a temperature rise, or a light source to induce a photochemical reaction.

In some embodiments, the flow marker is selected from the group consisting of a bubble, a semiconductor quantum dot, a polymer microbead, a fluorescent particle, a dye slug, and a scattering metal particle. In some embodiments, the microfluidic channel includes a flow measuring region for detecting the movement of the flow marker.

In some embodiments, the illumination system 112 is a laser. In other embodiments, the illumination system 112 is an LED. In some embodiments, illumination system 112 generates two sources of illumination, such as by using a beam splitting device, for measuring the movement of the flow marker at two measuring points within the channel. In other embodiments, illumination system 112 generates two measuring points from one light source, which may be a laser or an LED, by backside reflection, i.e., one of the measurement points is internal reflection from the chip 100. In some embodiments, the reflection is caused or enhanced by a reflective coating on one side of the chip 100. In some embodiments, the reflective coating on the chip 100 is co-integral with a flow measuring region within the channel. In some embodiments, detection system 113 includes a lens and a light detector. In some embodiments, the detection system comprises an imaging system such as, for example, a video frame rate camera. In some embodiments, flow calculation system 110 is a computer. In other embodiments, the computer also controls a data acquisition rate for detecting the movement of the flow marker.

Figure 2:
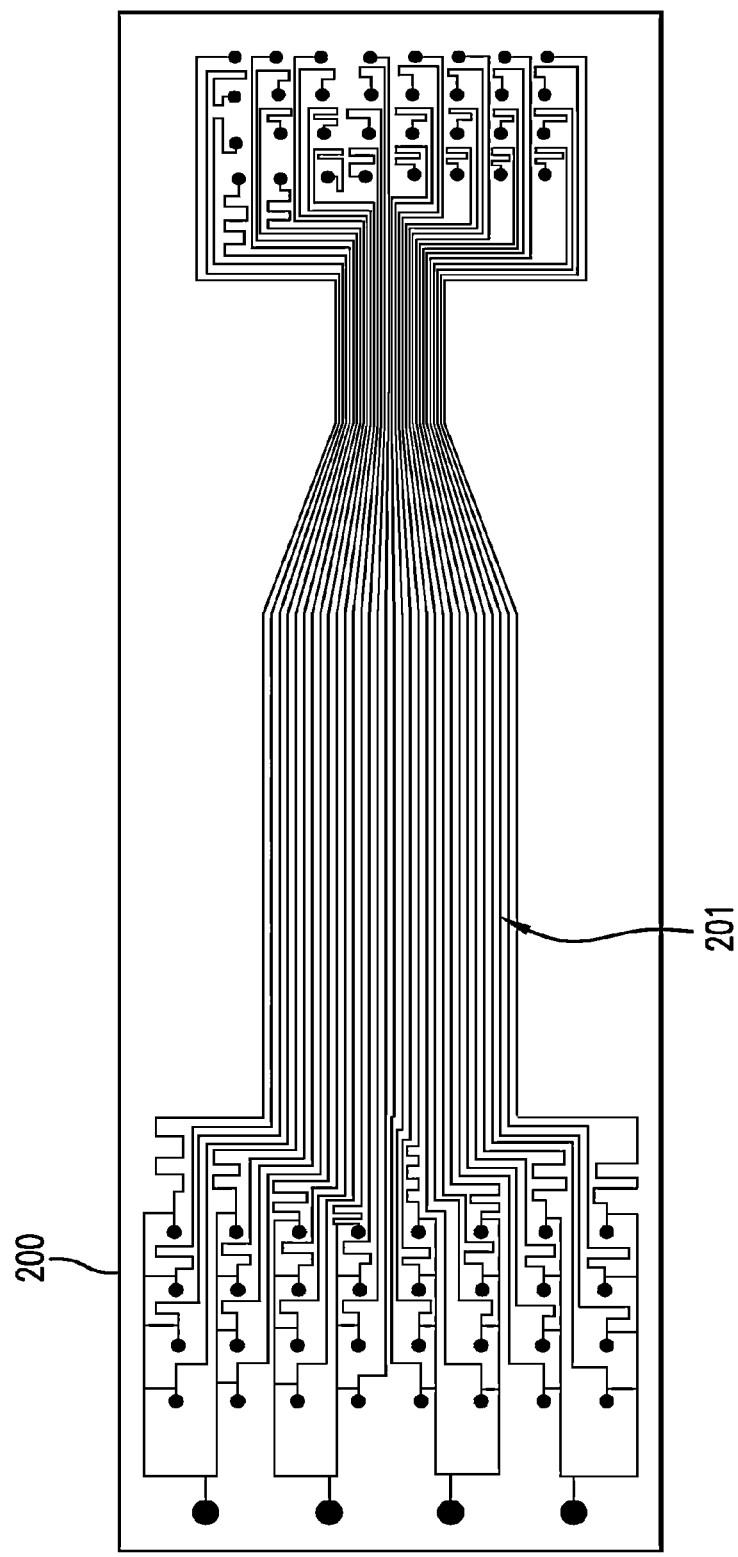
FIG. 2 shows a microfluidic device or chip that can be used in connection with the present invention.

One embodiment of a chip that can be used in conjunction with the present invention is illustrated in FIG. 2. Chip 200 includes a number of microfluidic channels 201. In the example shown, there are 32 microfluidic channels, but it is contemplated that chip 200 may have more or less than 32 channels. The chip can be modified as necessary by a skilled artisan to include a flow marker introduction system.

In some embodiments, the microchannel has a width of about 5 microns to about 500 microns and a depth of about 1 micron to about 100 microns. In other embodiments, the microchannel has a width of about 20 microns to about 400 microns and a depth of about 5 microns to about 50 microns. In additional embodiments, the microchannel has a width of about 30 microns to about 250 microns and a depth of about 10 microns to about 20 microns. In further embodiments, the microchannel has a width of about 150 microns and a depth of about 10 microns.

Figure 3:
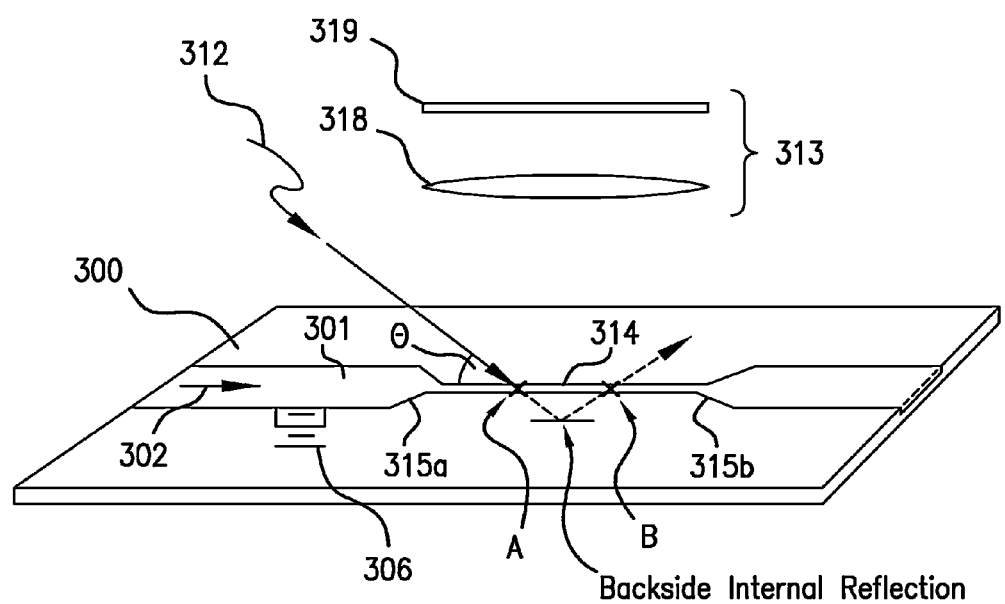
FIG. 3 is a diagram illustrating a system according to an embodiment of the present invention with respect to a microfluidic channel.

As shown in FIG. 3, chip 300 comprises at least one microchannel 301 in which it is desired to measure/monitor the flow rate 302 of the solution. As shown in this embodiment, the microchannel 301 includes a flow measuring region 314 which is narrower compared to the remainder of the channel. The flow measuring region 314 is narrower than the remainder of microchannel 301 to increase the velocity of the solution in this region, which may be desired to reduce the measuring time required to calculate flow rate/velocity. In some embodiments, a narrowed flow measuring region 314 is desired because the microfluidic flow may be very slow in certain applications. As shown in this figure, the flow measuring region 314 is demarcated by ends 315a, 315b.

In some embodiments, microchannel 301 has a width and depth as described herein. In some embodiments, the microchannel in the flow measuring region 314 has a width of about 5 microns to about 400 microns and a depth of about 1 micron to about 100 microns. In other embodiments, the microchannel in the flow measuring region 314 has a width of about 10 microns to about 200 microns and a depth of about 5 microns to about 50 microns. In additional embodiments, the microchannel in the flow measuring region 314 has a width of about 20 microns to about 100 microns and a depth of about 10 microns to about 20 microns. In further embodiments, the microchannel in the flow measuring region 314 has a width of about 40 microns and a depth of about 10 microns.

As further shown in FIG. 3, the system comprises a device 306 for injecting a bubble as a flow marker into microchannel 301. The device 306 may be a bubble generator, which may be either (a) a piezoelectric air injection nozzle or (b) a bubble jet nozzle generating intense heat causing a vapor bubble to form. If the bubble jet nozzle is used, it may be repetitively pulsed a rate, for example, of 1 Hz to 1 kHz to generate a bubble of known and controllable size/volume.

In one embodiment, the system further comprises a laser 312. The laser illuminates point A within flow measuring region 314. The laser is reflected from the backside of chip 300, and the laser reflection illuminates point B within flow measuring region 314. The reflective mechanism from the backside of microfluidic chip 300 is naturally caused by internal reflection resulting from the refractive index difference between the chip material and air. In some embodiments, the reflection is caused or enhanced by a reflective coating, such as, for example, a thin metallic layer or a multilayer dielectric coating, on one side of the chip 300. In some embodiments, the reflective coating on the chip 300 is co-integral with a flow measuring region 314 within the channel. In some embodiments, the angle of incidence ($\theta$) of the laser is from about 30 degrees to about 60 degrees. In another embodiment, the angle of incidence ($\theta$) of the laser is preferably about 45 degrees. The wavelength of the laser is typically one that is used for fluorescence excitation.

The optical signal caused by the bubble flowing past points A and B is detected with the detection system 313 which may comprise a lens 318 and a detector 319. Lens 318 and detector 319 may be commonly used fluorescence imaging devices or other known imaging devices, such as, for example, a two dimensional CCD or CMOS image sensor.

The flow velocity and flow rate are calculated by the calculation system. The flow velocity is calculated by measuring the transit time between points A and B in view of the known distance between points A and B, and the flow rate is calculated once the flow velocity is known. The flow velocity and flow rate can be calculated in accordance with the following equations.

Flow Velocity=(distance $A$ to $B$)/transit time

Flow Rate=(channel width×channel depth)(flow velocity)

In operation, a flow bubble is injected by device 306 into the microfluidic channel 301. The bubble flows down the channel and is illuminated, briefly, by laser 312 at point A. As the bubble flows downstream it is later illuminated by the laser reflection at point B at which point the bubble exits the flow measuring region 314 into the remaining portion of the microchannel. The optical signal caused by the bubble flowing past the laser illumination points is detected with external measuring equipment lens 318 and detector 319. The flow velocity and flow rate are calculated as described herein.

Figure 4:
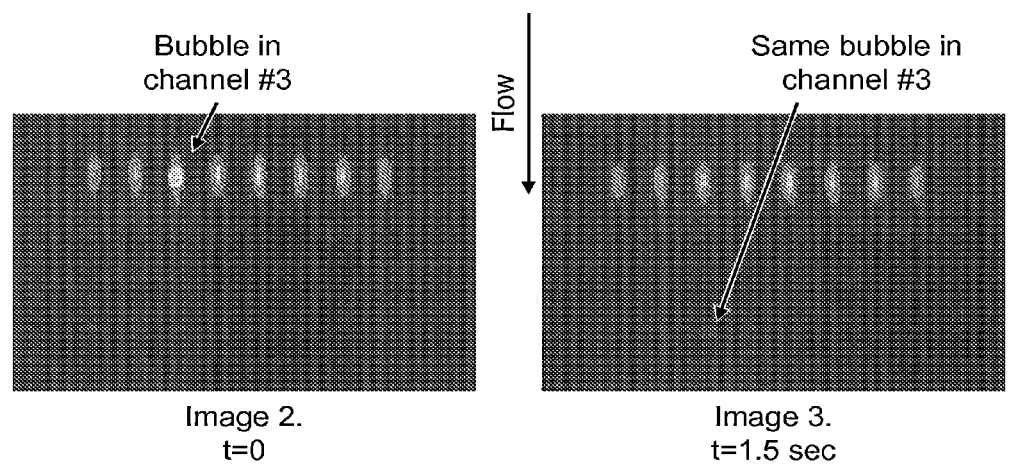
FIG. 4 shows images recorded during a PCR experiment in a microfluidic channel in which an air bubble is shown in the main line of laser illumination.

FIG. 4 shows an example of data from an embodiment of the present invention. In this example, a 488 nm solid state laser was used. The detector that was used was an EMCCD amplified imaging detector with a resolution of 658×496 pixels manufactured by Andor Technology. Image 2 and Image 3 represent data from this experiment where the bubble imaging phenomena was observed. Image 2 shows the bubble entering the main line of laser illumination and can be seen as the bright spot in microfluidic channel number 3. The faint spots that are visible at the bottom edge of Image 2 are internal reflection spots. Image 3 was an imaged acquired time delayed from Image 2 (approximately 1.5 seconds). Thus the bubble has traversed the distance in the microfluidic channel and is visible by the internal reflection energy of the incident laser beam.

The images are processed using imaging software that can integrate the pixel values over a programmed region (area) of interest (ROI). The ROI data plotted vs. time is then analyzed to find the peak signal of when bubble flows past. The peak values are the trigger points to making a timing measurement. Normal optical fluctuations are time filtered from bubbles (which have a faster time constant), using time bandpass algorithms well known in the art.

Figure 5:
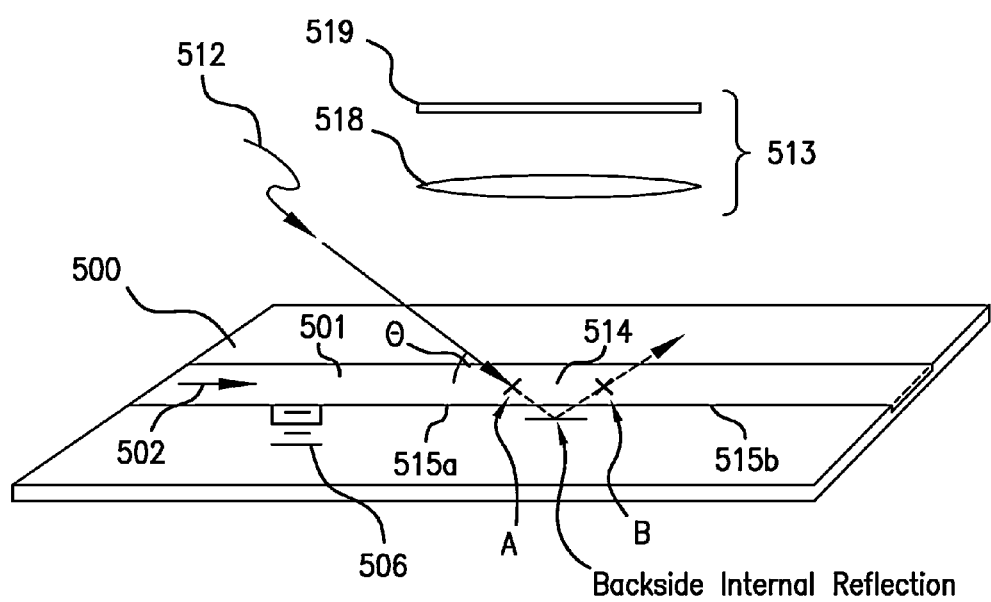
FIG. 5 is a diagram illustrating a system according to an additional embodiment of the present invention with respect to a microfluidic channel.

Another embodiment of the present invention is shown in FIG. 5. Chip 500 comprises at least one microchannel 501 in which it is desired to measure/monitor the flow rate 502. As shown in this embodiment, the microchannel 501 includes a flow measuring region 514 which is not narrowed. As shown in this figure, the flow measuring region 514 is demarcated by ends 515a, 515b. As further shown in FIG. 5, the system comprises a device 506 for injecting a bubble as a flow marker into microchannel 501. The device may be a bubble generator which may be as described herein. The system further comprises a laser 512. The laser illuminates point A within flow measuring region 514. The laser is reflected from the backside of chip 500, and the laser reflection illuminates point B within flow measuring region 514. The reflective mechanism may be caused as described herein. The angle of incidence (θ) of the laser may be as described herein. The optical signal caused by the bubble flowing past points A and B is detected with the detection system 513 which may comprise a lens 518 and a detector 519. Lens 518 and detector 519 may be as described herein. The flow velocity and flow rate are calculated as described herein.

Figure 6:
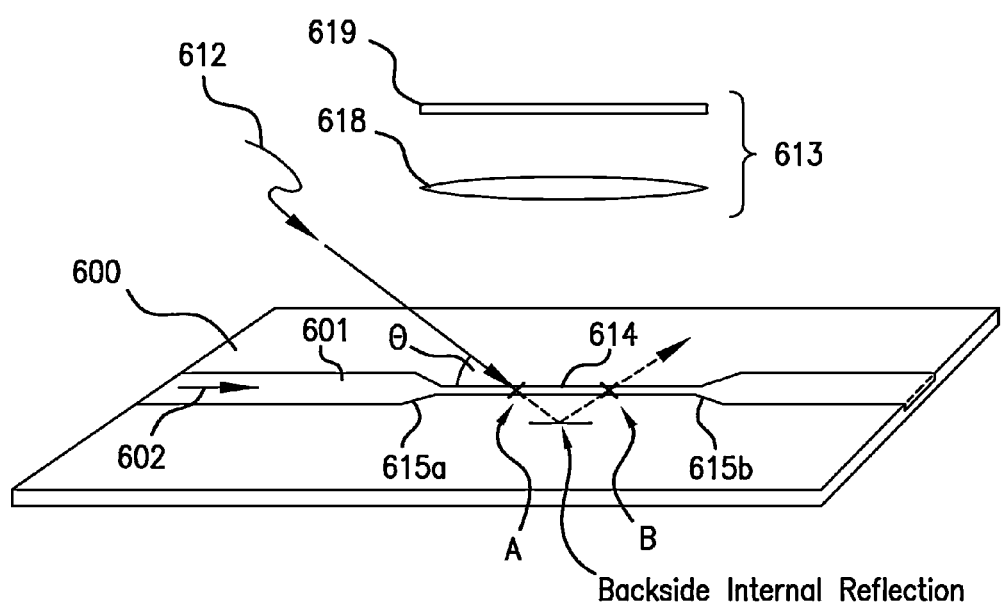
FIG. 6 is a diagram illustrating a system according to a further embodiment of the present invention with respect to a microfluidic channel.

Another embodiment of the present invention is shown in FIG. 6. Chip 600 comprises at least one microchannel 601 in which it is desired to measure/monitor the flow rate 602. As shown in this embodiment, the microchannel 601 includes a flow measuring region 614 which is narrower than the remainder of the channel. As shown in this figure, the flow measuring region 614 is demarcated by ends 615a, 615b. As further shown in FIG. 6, the system further comprises a laser 612. The laser illuminates point A within flow measuring region 614. The laser is reflected from the backside of chip 600, and the laser reflection illuminates point B within flow measuring region 614. The reflective mechanism may be caused as described herein. The angle of incidence (θ) of the laser may be as described herein. The optical signal caused by the maker flowing past points A and B is detected with the detection system 613 which may comprise a lens 618 and a detector 619. Lens 618 and detector 619 may be as described herein. The flow velocity and flow rate are calculated as described herein. In this embodiment, the marker may be a bubble, a semiconductor quantum dot, a polymer microbead, a fluorescent particle and a scattering metal particle that is introduced into the microchannel 601. The marker may be introduced into the microchannel 601 by, for example, a sipper (not shown) that is part of chip 600, as is common in the art, or is utilized in combination with chip 600, as is common in the art.

The present invention also provides a method of monitoring flow velocity and flow rate in channels. In some embodiments, the method comprises moving a solution through a microfluidic channel in a chip, introducing a flow marker into the channel, illuminating the channel at two measuring points, measuring the movement of the flow marker within the channel between the two measuring points and correlating the optical flow marker movement velocity to flow rate. In some embodiments, the microchannel has the dimensions described herein. In some embodiments, the movement of the flow marker is measured in a flow measuring region of the channel. In some embodiments, the flow measuring region of the channel is the same width as the channel. In other embodiments, the flow measuring region of the channel is narrower compared to the remainder of the channel. In some embodiments, the dimensions of the microchannel in the narrowed flow measuring region have the dimensions described herein.

In some embodiments, the flow marker is selected from the group consisting of a bubble, a semiconductor quantum dot, a polymer microbead, a fluorescent particle and a scattering metal particle. In some embodiments, the flow marker is a bubble that is introduced into the channel by injection, and the bubble is injected air formed by a piezoelectric nozzle. In other embodiments, the flow marker is a bubble that is formed by a bubble jet head to produce a vapor bubble. In further embodiments, the flow marker is a bubble, a semiconductor quantum dot, a polymer microbead, a fluorescent particle and a scattering metal particle that is introduced into the channel by a sipper.

In some embodiments, the illumination of the two measuring points is generated from one light source by a backside reflection. In some embodiments, the light source is a laser. In other embodiments, the light source is an LED. In some embodiments, one of the illumination points is internal reflection from the chip. In some embodiments, the reflection is caused naturally from the backside of the chip by internal reflection caused by the refractive index difference between the chip material and air. In other embodiments, the reflection is caused or enhanced by a reflective coating on one side of the chip. In additional embodiments, the reflective coating on the chip is co-integral with a flow measuring region within the channel. In some embodiments, the angle of incidence of the illumination is from about 30 degrees to about 60 degrees. In another embodiment, angle of incidence of the illumination is preferably about 45 degrees.

In some embodiments, the measurement of the flow marker within the channel involves fluorescence. In other embodiments, the illumination is an excitation signal. In some embodiments, the optical excitation signal is a laser which generates two sources of illumination for measuring the movement of the flow marker at two points within a flow measuring region within the channel. The two sources of illumination can be created by using a beam splitting device. In some embodiments, detection system comprises a lens and a detector. In some embodiments, the optical detection involves an optical signal that is scatter and/or reflection that is resolvable from natural background signal.

In some embodiments, the calculation of velocity and the correlation of velocity to flow rate are performed by a computer. In some embodiments, the computer also controls a data acquisition rate for measuring the movement of the flow marker. In other embodiments, the flow rate measurement is part of a feedback loop for regulating the flow rate.

Figure 7:
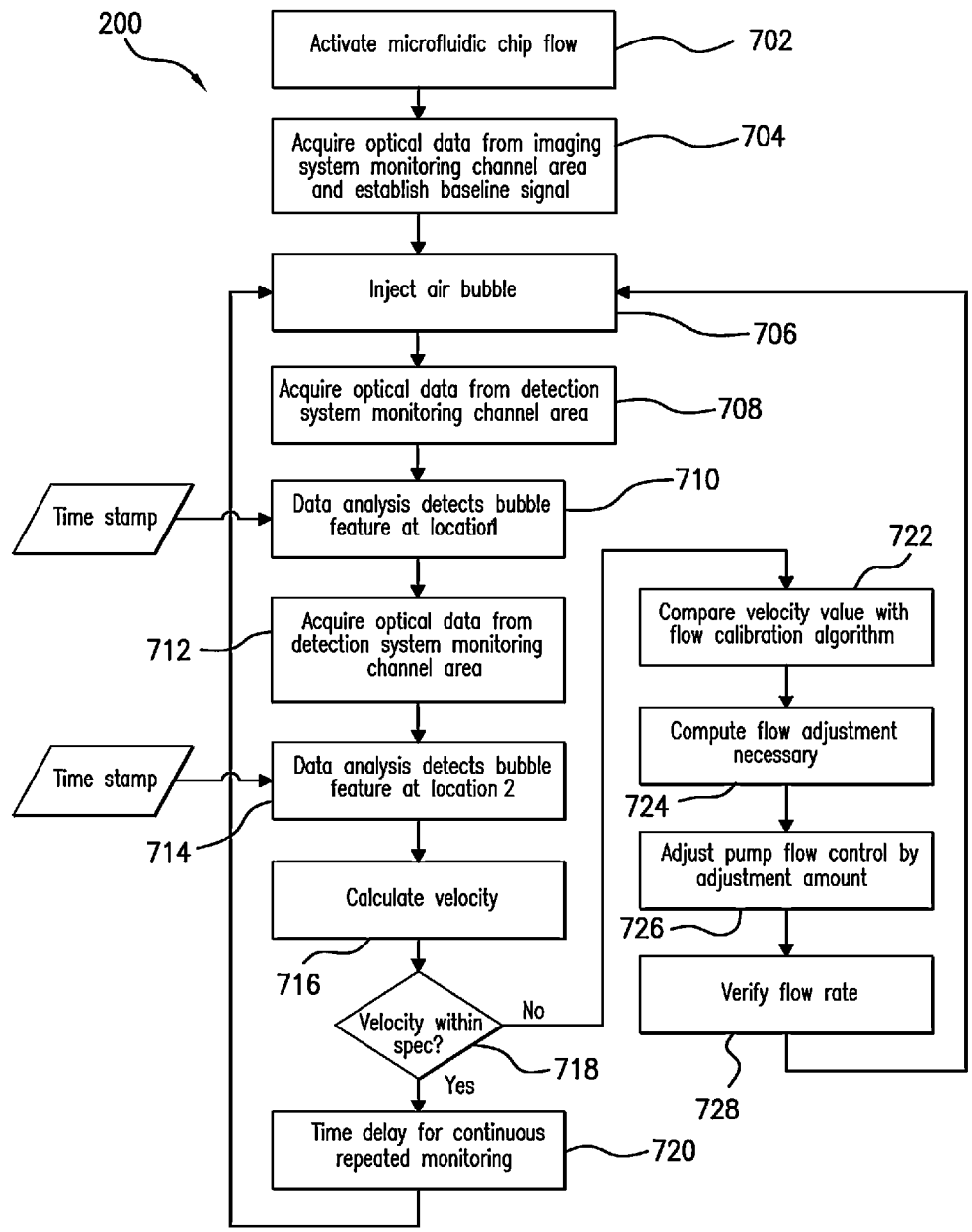
FIG. 7 is a flow chart illustrating a process in accordance with an embodiment of the present invention.

FIG. 7 is a flow chart illustrating a process 700 in accordance with an embodiment of the present invention. Process 700 may begin in step 702, where fluid flow in chip 100 having at least one microchannel is activated by fluid movement system 104. In step 704, optical data is acquired from the detection system 113 which is set to monitor a channel area, sometimes referred to as a flow measuring region herein, and a baseline signal is established. In step 706, an air bubble is introduced into the channel by the flow marker introduction system 106.

In step 708, optical data is acquired from the detection system 113. Analysis of the data in step 710 detects features of the bubble at location 1 and first time stamp is associated with this detection.

In step 712, optical data is acquired from the detection system 113. Analysis of the data in step 714 detects features of the bubble at location 2 and second time stamp is associated with this detection.

In step 716, the flow velocity of the fluid is calculated by the fluid calculation system 110 and the flow rate of the fluid may also be calculated. The flow velocity and/or the flow rate is then queried in step 718 to determine if they are within the specs for the reactions being performed in the channel. If the answer to the query in step 718 is yes, step 720 provides a time delay for continuous repeated monitoring by initiating step 706 after the appropriate time delay.

If the answer to the query in step 718 is no, step 722 is initiated. In step 722, the flow velocity value is compared with a flow calibration algorithm. The necessary flow adjustment is computed in step 724. In step 726, the fluid flow is adjusted by the fluid movement system 104 by the necessary adjustment amount. In step 728, the flow rate is verified by initiating step 706.

The present invention has several advantages. For example, these aspects of the present invention include: (1) using inert material, such as bubbles, injected into a microfluidic flow path; (2) utilizing the property of internal reflections to create a second measurement zone, thus having a simpler optical design; (3) utilizing a flow measurement optical system that can be shared with the same optical system which has another main purpose, e.g., monitoring fluorescence in real-time PCR; and (4) utilizing a flow measuring system that is wavelength independent when a bubble is used.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Moreover, any combination of the above-described elements in all possible variations thereof is encompassed by the invention unless otherwise indicated herein or otherwise clearly contradicted by context.

What is claimed is:

1. A method of monitoring a solution flow in a microfluidic channel comprising:
    (a) moving a solution through the microfluidic channel in a chip to fill the channel with a solution and stop the solution flow to thermally cycle the entire length of the channels to perform a polymerase chain reaction (PCR) on the solution flow when the solution flow is stopped;
    (b) introducing a flow marker into the channel;
    (c) illuminating the channel at two measuring points; and
    (d) measuring the movement of the flow marker within the channel between the two measuring points.

2. The method of claim 1, wherein the illumination of the two measuring points is generated from one light source by a backside reflection.

3. The method of claim 1, wherein light source is laser.

4. The method of claim 1, wherein light source is a light emitting diode (LED).

5. The method of claim 1, wherein the reflection is caused or enhanced by a reflective coating on one side of the chip.

6. The method of claim 5, wherein the reflective coating on the chip is co-integral with a flow measuring region within the channel.

7. The method of claim 1, wherein the angle of incidence of the illumination is about 30 degrees to about 60 degrees.

8. The method of claim 7, wherein the angle of incidence of the illumination is about 45 degrees.

9. The method of claim 1, wherein the movement of the flow marker is measured in a flow measuring region of the channel.

10. The method of claim 9, wherein the flow measuring region of the channel is narrower compared to the remainder of the channel.

11. The method of claim 1, wherein the flow marker is selected from the group consisting of a bubble, a semiconductor quantum dot, a polymer microbead, a fluorescent particle, a dye slug and a scattering metal particle.

12. The method of claim 11, wherein the flow marker is a bubble that is introduced into the channel by injection, and the bubble is injected air formed by a piezoelectric nozzle.

13. The method of claim 11, wherein the flow marker is a bubble that is formed by a bubble jet head to produce a vapor bubble.

14. The method of claim 1, wherein the microchannel has a width of about 5 microns to about 500 microns and a depth of about 1 micron to about 100 microns.

15. The method of claim 14, wherein the microchannel has a width of about 20 microns to about 400 microns and a depth of about 5 microns to about 50 microns.

16. The method of claim 14, wherein the microchannel has a width of about 30 microns to about 250 microns and a depth of about 10 microns to about 20 microns.

17. The method of claim 14, wherein the microchannel has a width of about 150 microns and a depth of about 10 microns.

18. The method of claim 9, wherein the microchannel in the flow measuring region has a width of about 5 microns to about 400 microns and a depth of about 1 micron to about 100 microns.

19. The method of claim 18, wherein the microchannel in the flow measuring region has a width of about 10 microns to about 200 microns and a depth of about 5 microns to about 50 microns.

20. The method of claim 18, wherein the microchannel in the flow measuring region has a width of about 20 microns to about 100 microns and a depth of about 10 microns to about 20 microns.

21. The method of claim 18, wherein the microchannel in the flow measuring region has a width of about 40 microns and a depth of about 10 microns.

22. The method of claim 1, wherein the measurement of the movement of the flow marker involves fluorescence.

23. The method of claim 22, wherein the illumination is an excitation signal.

24. The method of claim 1, wherein the microfluidic channel is fabricated of optically clear glass, quartz or plastic.

25. The method of claim 1, wherein the computer also controls a data acquisition rate for measuring the movement of the flow marker.

26. The method of claim 1, further comprising thermally cycling the entire length of the channels to perform a PCR reaction on the solution flow when the solution flow is stopped, wherein the PCR reaction is followed by a melt analysis performed on the stopped solution flow.

\* \* \* \* \*